(12) United States Patent
Truschel et al.

(10) Patent No.: US 7,044,129 B1
(45) Date of Patent: May 16, 2006

(54) PRESSURE SUPPORT SYSTEM AND METHOD

(75) Inventors: William A. Truschel, Oakmont, PA (US); Winslow K. Duff, Export, PA (US); Michael T. Kane, Harrison City, PA (US); Andrew L. Shissler, Delmont, PA (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 10/930,025

(22) Filed: Aug. 30, 2004

Related U.S. Application Data

(60) Provisional application No. 60/499,801, filed on Sep. 3, 2003.

(51) Int. Cl.
*A61M 16/00* (2006.01)
*A62B 7/00* (2006.01)

(52) U.S. Cl. .......................... 128/204.23; 128/204.18; 128/204.23

(58) Field of Classification Search ........... 128/204.18, 128/204.21, 204.23, 204.26, 202.22, 205.23, 128/207.12
See application file for complete search history.

(56) References Cited

U.S. PATENT DOCUMENTS

| | | | |
|---|---|---|---|
| 5,044,362 A | 9/1991 | Younes | |
| 5,107,830 A | 4/1992 | Younes | |
| 5,148,802 A | 9/1992 | Sanders et al. | |
| 5,203,343 A | 4/1993 | Axe et al. | |
| 5,313,937 A | 5/1994 | Zdrojkowski et al. | |
| 5,433,193 A | 7/1995 | Sanders et al. | |
| 5,458,137 A | 10/1995 | Axe et al. | |
| 5,535,738 A | 7/1996 | Estes et al. | |
| 5,535,739 A * | 7/1996 | Rapport et al. | 128/204.23 |
| 5,551,419 A * | 9/1996 | Froehlich et al. | 128/204.23 |
| 5,632,269 A | 5/1997 | Zdrojkowski et al. | |
| 5,645,053 A | 7/1997 | Remmers et al. | |
| 5,694,923 A * | 12/1997 | Hete et al. | 128/204.18 |
| 5,794,615 A | 8/1998 | Estes et al. | |
| 5,803,065 A | 9/1998 | Zdrojkowski et al. | |
| 5,947,115 A * | 9/1999 | Lordo et al. | 128/200.24 |
| 6,029,664 A | 2/2000 | Zdrojkowski et al. | |
| 6,085,747 A | 7/2000 | Axe et al. | |
| 6,105,575 A | 8/2000 | Estes et al. | |
| 6,286,508 B1 | 9/2001 | Remmers et al. | |
| 6,305,374 B1 | 10/2001 | Zdrojkowski et al. | |
| 6,367,474 B1 * | 4/2002 | Berthan-Jones et al. | 128/204.23 |
| 6,401,713 B1 * | 6/2002 | Hill | 128/204.21 |
| 6,532,956 B1 * | 3/2003 | Hill | 128/204.18 |
| 6,539,940 B1 | 4/2003 | Zdrojkowski et al. | |
| 6,550,478 B1 | 4/2003 | Remmers et al. | |
| 6,622,724 B1 * | 9/2003 | Truitt et al. | 128/204.18 |
| 6,626,175 B1 * | 9/2003 | Jafari et al. | 128/204.21 |
| 6,644,311 B1 * | 11/2003 | Truitt et al. | 128/204.22 |
| 6,752,151 B1 | 6/2004 | Hill | |
| 6,849,049 B1 * | 2/2005 | Starr et al. | 600/538 |

* cited by examiner

*Primary Examiner*—Henry Bennett
*Assistant Examiner*—Shumaya B. Ali
(74) *Attorney, Agent, or Firm*—Michael W. Haas

(57) ABSTRACT

A pressure generating system and method for generating a flow of fluid at a pressure above atmospheric pressure. The system includes a pressure generator and a pressure regulator downstream of the pressure generator. The system monitors a characteristic associated with the pressure regulator, the fluid flow downstream of the pressure regulator to the patient, the fluid flow upstream of the pressure regulator, the fluid flow exhausted from the pressure regulator, or any combination thereof. A controller coupled to the pressure generator controls an operating speed of the pressure generator based on the monitored characteristic(s) so that the output of the pressure generator is only kept as high as needed to provide the desired pressure to the patient.

31 Claims, 6 Drawing Sheets

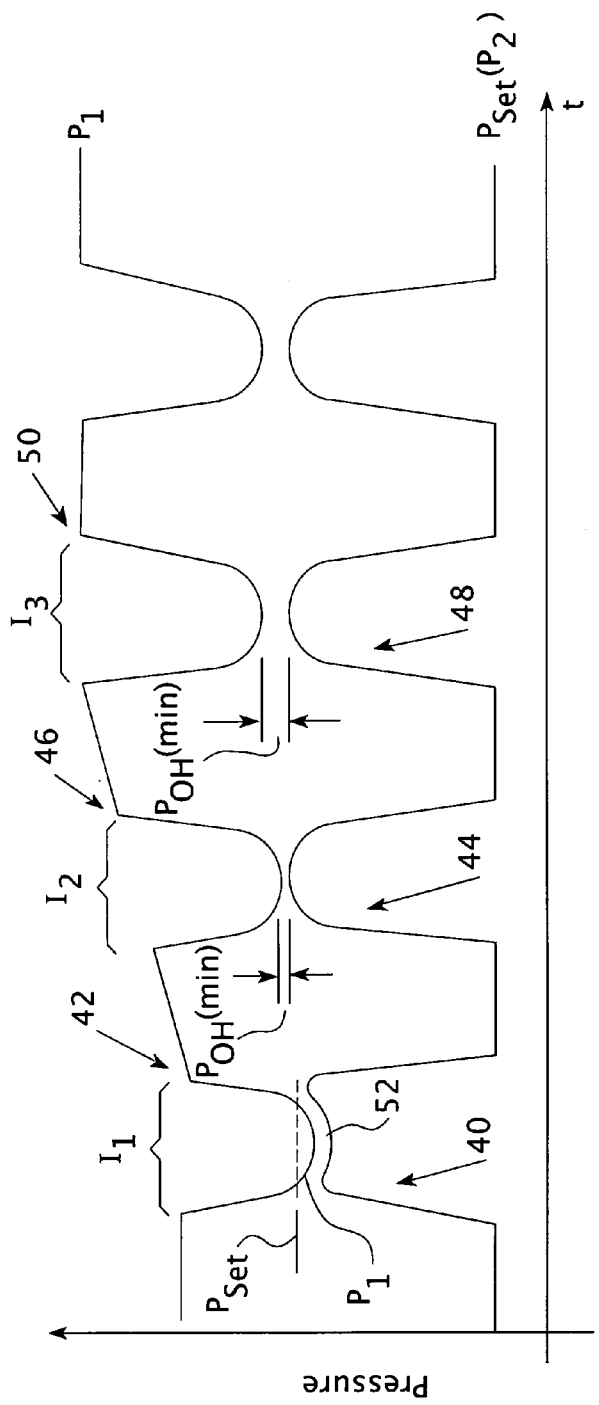
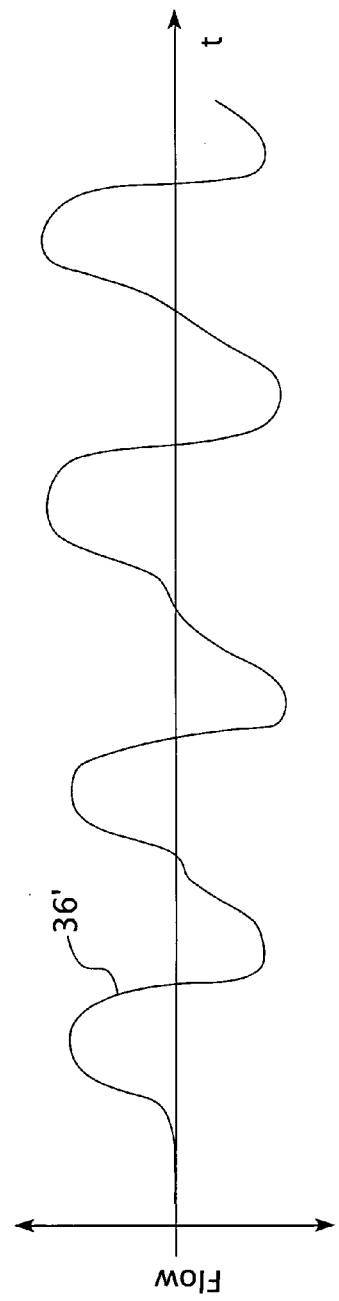
FIG. 4A
FIG. 4B

PRESSURE SUPPORT SYSTEM AND METHOD

CROSS-REFERENCE TO RELATED APPLICATIONS

This application claims priority under 35 U.S.C. § 119(e) from provisional U.S. patent application No. 60/499,801 filed Sep. 3, 2003, the contents of which are incorporated herein by reference.

BACKGROUND OF THE INVENTION

1. Field of the Invention

The present invention pertains to a system and method for providing a pressure support therapy to a patient, and, in particular, to a pressure support system and method of operating such a system that minimizes the operating speed of the pressure generating component of the system.

2. Description of the Related Art

It is well known to treat a breathing disorder, such as obstructive sleep apnea (OSA), with a pressure support device, such as a continuous positive airway pressure (CPAP) device. A CPAP device delivers a flow of fluid to the airway of the patient throughout the patient's breathing cycle in order to "splint" the airway, thereby preventing its collapse during sleep. The term "fluid" as used herein refers to any gas, including a gas mixture or a gas with particles, such as an aerosol medication, suspended therein. Most commonly, the fluid delivered to a patient by a pressure support system is pressured air. An example of such a CPAP device is the REMstar® and Solo® family of CPAP devices manufactured by Respironics, Inc. of Pittsburgh, Pa.

It is also known to provide a bi-level positive pressure therapy in which the pressure of fluid delivered to the patient's airway varies or is synchronized with the patient's breathing cycle to maximize the therapeutic effect and comfort to the patient. An example of a pressure support device that provides "bi-level" pressure support, in which a lower pressure is delivered to that patient during the patient's expiratory phase than during the inspiratory phase, is the BiPAP® family of devices manufactured and distributed by Respironics, Inc. of Pittsburgh, Pa. Such a bi-level mode of pressure support is taught, for example, in U.S. Pat. Nos. 5,148,802 to Sanders et al., 5,313,937 to Zdrojkowski et al., 5,433,193 to Sanders et al., 5,632,269 to Zdrojkowski et al., 5,803,065 to Zdrojkowski et al., 6,029,664 to Zdrojkowski et al., 6,305,374 to Zdrojkowski et al., and 6,539,940 to Zdrojkowski et al., the contents of each of which are incorporated by reference into the present invention.

It is further known to provide an auto-titration positive pressure therapy in which the pressure provided to the patient changes based on the detected conditions of the patient, such as whether the patient is snoring or experiencing an apnea, hypopnea, cheynes-stokes respiration, or upper airway resistance. An exemplary auto-titration pressure support mode is taught, for example, in U.S. Pat. Nos. 5,203,343; 5,458,137 and 6,085,747 all to Axe et al., the contents of which are incorporated herein by reference. An example of a device that adjusts the pressure delivered to the patient based on whether or not the patient is snoring is the Virtuoso® CPAP family of devices manufactured and distributed by Respironics, Inc. An example of a pressure support device that actively tests the patient's airway to determine whether obstruction, complete or partial, could occur and adjusts the pressure output to avoid this result is the Tranquility® Auto CPAP device and REMStar Auto CPAP device, also manufactured and distributed by Respironics, Inc. This auto-titration pressure support mode is taught in U.S. Pat. Nos. 5,645,053 and 6,286,508 6,550, 478 all to Remmers et al., the content of which is also incorporated herein by reference.

Other pressure support systems that offer other modes of providing positive pressure to the patient are also known. For example, a proportional assist ventilation (PAV®) mode of pressure support provides a positive pressure therapy in which the pressure of gas delivered to the patient varies with the patient's breathing effort to increase the comfort to the patient. U.S. Pat. Nos. 5,044,362 and 5,107,830 both to Younes, the contents of which are incorporated herein by reference, teach a pressure support device capable of operating in a PAV mode. Proportional positive airway pressure (PPAP) devices deliver breathing gas to the patient based on the flow generated by the patient. U.S. Pat. Nos. 5,535,738; 5,794,615; and 6,105,575 all to Estes et al., the contents of which are incorporated herein by reference, teach a pressure support device capable of operating in a PPAP mode. In the PAV and PPAP pressure support systems, the percent of assistance provided by the unit is at least one of the operating features of the pressure support device that is set after the device has been prescribed for use by a patient.

A typical conventional pressure support system 10 is shown in FIG. 1. Such a system includes a pressure generator 12 that receives a supply of gas from a gas source, such as ambient atmosphere, as indicated by arrow A, and creates a flow of breathing gas, as indicated by arrows B, having a pressure greater than the ambient atmospheric pressure. Pressure generator 12 typically includes a motor driving a blower, which is an impeller within a housing, for placing the gas from the gas source under pressure relative to ambient atmosphere. A valve 13 downstream of pressure generator 12 bleeds off excess pressure/flow from the patient circuit, as indicated by arrow C, by communicating a portion of the gas at the output of pressure generator 12 to ambient atmosphere. Other conventional exhaust valves divert all or some of the exhaust gas back to the inlet of the pressure generator.

A patient circuit 14, which is typically a flexible conduit, delivers the elevated pressure breathing gas to the airway of a patient 15. Typically, the patient circuit is a single limb conduit or lumen having one end coupled to the pressure generator and a patient interface device 16 coupled to the other end. Patient interface device 16 connects patient circuit 14 with the airway of patient 15 so that the elevated pressure gas flow is delivered to the patient's airway. Examples of patient interface devices include a nasal mask, nasal and oral mask, full face mask, nasal cannula, oral mouthpiece, tracheal tube, endotracheal tube, or hood. A single limb patient circuit shown in FIG. 1 includes an exhalation port 18, also referred to as an exhalation vent, exhaust port, or exhaust vent, to allow gas, such as expired gas from the patient, to exhaust to atmosphere, as indicated by arrow C. Generally, exhaust vent 18 is located in patient circuit 14 near patient interface device 16 or in the patient interface device itself.

More sophisticated pressure support devices include a flow sensor 20, pressure sensor 22, or both to monitor the flow and/or pressure of gas in patient circuit 14. The flow information can be used to determine the volume of gas passing through patient circuit 14. The information from flow sensor 20 and/or pressure sensor 22 is provided to a controller 24, which uses it for any conventional purpose, for example, to control the pressure or flow of gas provided to the patient, monitor the condition of the patient, monitor the usage of the pressure support device (patient compliance), or any combination thereof. An input/output device 26 communicates with controller 24 to provide data, commands, and other information between a user or other entity and the controller.

In a conventional CPAP system, the pressure output by the blower varies with the rate of flow in the patient circuit, assuming that the blower operates at a constant speed. For example, at a certain operating speed, the pressure in the patient circuit or patient interface decreases as the flow of gas in the patient circuit or at the patient interface increases. This occurs, for example, as the patient breathes into the patient circuit. For this reason, a conventional CPAP pressure support system typically uses valve 13 to regulate the pressure delivered to the patient by means of controller 24.

Devices that provide a bi-level positive pressure therapy, an auto-titrating pressure level, PAV, PPAP, or any other mode of pressure support where the pressure delivered to the patient's airway varies, also include a pressure/flow control system to vary the pressure delivered to the patient in accordance with the pressure support mode. A typical pressure/flow control system used in such devices includes the pressure/generator and valve combination shown in FIG. 1.

Pressure support systems that include the pressure/generator and valve combination typically operate the blower at a substantially constant speed that is sufficient to deliver a pressure in excess of the selected pressure to be delivered to the patient. That is, the pressure output by the blower, which is referred to as the "deadhead pressure", must be high enough above the selected pressure, or range of pressure, to deliver the prescribed pressure to the patient's airway. Moreover, because it is not known at what air density any given pressure support system will be operated, each system is typically preprogrammed during manufacture to operate at an output pressure that is sufficient to account for the lowest air density in which the unit will be operated, such as at a high elevation, a lower barometric pressure, high temperature, or a high humidity.

It can be appreciated that operating the pressure generator to compensate for the worst case scenario requires outputting much more pressure than needed from the pressure generator. Moreover, bleeding off excess pressure or flow from the patient circuit via the exhaust valve is relatively noisy, especially in light of the fact that pressure generator is operating at a high speed, which itself adds to the machine noise.

SUMMARY OF THE INVENTION

Accordingly, it is an object of the present invention to provide a pressure support system that overcomes the shortcomings of conventional systems. This object is achieved according to one embodiment of the present invention by providing a pressure generator system that includes a pressure generator that generates a flow of fluid at a pressure above atmospheric pressure. A conduit is coupled to the output of the pressure generator and a pressure sensor is coupled to the conduit at a first location. A valve is operatively coupled to the conduit between the pressure sensor and the end of the conduit. A controller controls actuation of the valve based on a set pressure to be delivered to a patient and controls the operating speed of the pressure generator based on an output of the pressure sensor and the set pressure to ensure that the output pressure is maintained at a minimum and yet provides the desired output pressure to the patient.

It is yet another object of the present invention to provide a method of providing pressure support to a patient that does not suffer from the disadvantages associated with conventional pressure support techniques. This object is achieved by providing a method that includes (1) generating a flow of fluid at a pressure above atmospheric pressure via a pressure generator for delivery to a patient, (2) controlling a pressure of the flow of fluid delivered to the patient via a pressure control element so that a pressure delivered to an airway of a patient corresponds to a set pressure, and (3) controlling an operating speed of the pressure generator to provide a pressure at an inlet of the pressure control element at a level sufficient to deliver the set pressure. This method ensures that the pressure provided by the pressure generator to the pressure control element is maintained at a level that is only high enough to satisfy the pressure support therapy, thereby reducing the wasteful and noisy exhausting of gas from the system.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

BRIEF DESCRIPTION OF THE DRAWINGS

FIGS. 4A–5B are further exemplary pressure and flow graphs illustrating the operation of the system of FIG. 2.

DETAILED DESCRIPTION OF THE PRESENTLY PREFERRED EMBODIMENTS OF THE INVENTION

Figure 1:
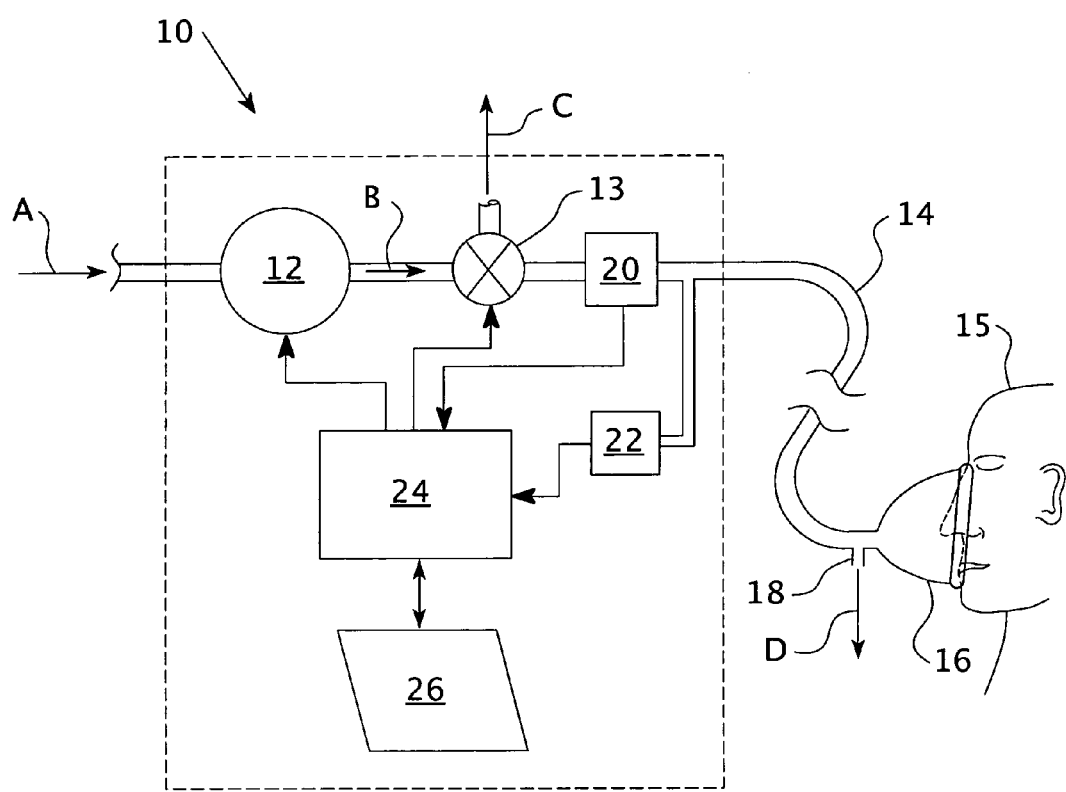
FIG. 1 is a schematic diagram of a conventional pressure support system.
Figure 2:
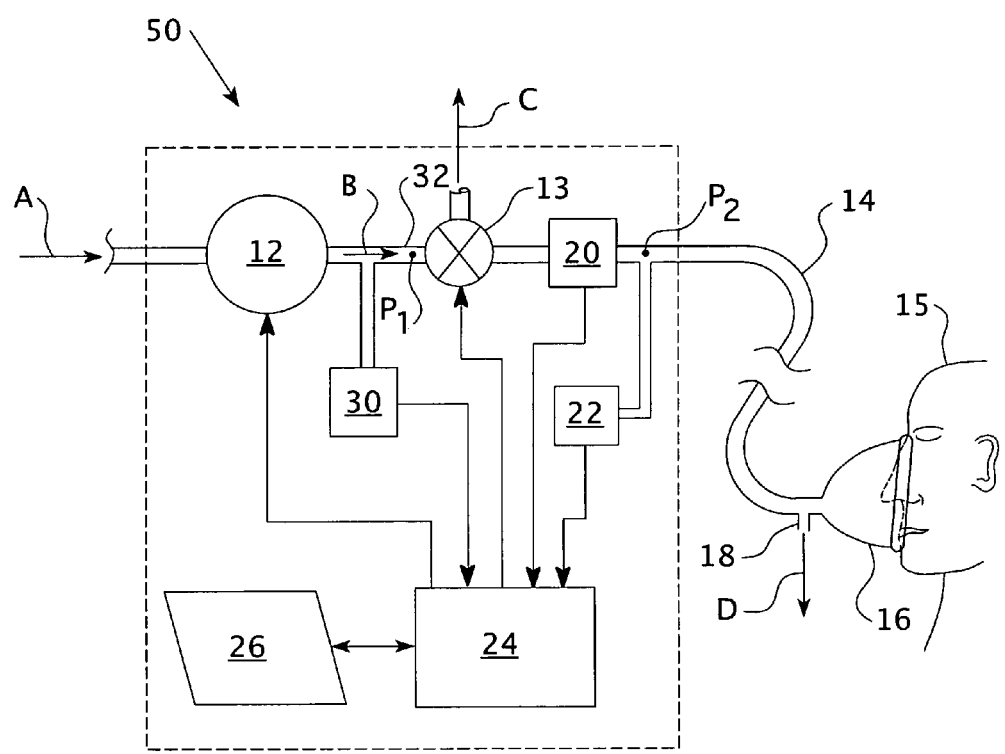
FIG. 2 is a schematic diagram of a pressure support system according to the principles of the present invention.

FIG. 2 schematically illustrates an exemplary embodiment of a pressure support system 50 according to the principles of the present invention. The features of the present invention in common with those of conventional pressure support systems, as shown, for example, in FIG. 1, are delineated with like reference numerals.

Pressure support system 50 employs valve 13 to regulate the pressure output from pressure generator 12 so that the desired pressure level is delivered to the patient. It should be noted that this pressure level can be constant, as in the case of a CPAP system or varying, as in the case of bi-level, PAV, PPAP, or auto-titration pressure support system. Valve 13 acts as a 3-way pressure regulator that pneumatically connects the patient's airway in proportional amounts between the outlet pressure or the pressure generator and atmospheric conditions. The pressure to be delivered to the patient is referred to as the set pressure "$P_{SET}$".

In an ideal pressure support system, the pressure at the outlet of valve 13 always corresponds to $P_{SET}$ (assuming that the pressure generator is operating at a sufficient speed to provide this pressure, and bearing in mind any pressure drop that occurs from the outlet of the valve to the airway of the patient). For example, in a simple CPAP system, the pressure to be delivered to the patient $P_{SET}$ is the CPAP level, which is typically input into the device via an input interface 26 once the patient has be prescribed a pressure level. The same is true for a simple bi-level system, where $P_{SET}$ corresponds to the IPAP and EPAP settings input into the system.

In more complicated pressure support systems, such as PAV, PPAP, or auto-titration pressure support system, as well as CPAP and bi-level systems with a pressure ramp function or other pressure control, the pressure to be delivered to the patient $P_{SET}$ is determined, at least in part, by calculations made within controller 24. Thus, $P_{SET}$ can be a fixed value (CPAP, IPAP, EPAP) or it can be a determined valued based on any one of a variety of inputs, as is the case with a PAV, PPAP, or auto-titration pressure support system.

The pressure output to the patient varies with many parameters, including, but not limited to, the rate of flow in the patient circuit. Therefore, it is difficult, if not impossible, under normal operating conditions, to achieve a pressure support system, where the output pressure from the valve is equal to $P_{SET}$ without directly measuring the outlet pressure of the valve and using this measured pressure in a feedback fashion. For this reason, a typical pressure support system includes pressure sensor 22 at the outlet of valve 13 to monitor the pressure $P_2$ at the outlet of the valve. The output of pressure sensor 22 is provided to controller 24, which controls valve 13 so that the pressure at the outlet of the valve $P_2$ equals $P_{SET}$. Using this feedback control technique, controller 24 continuously adjusts valve 13 so that $P_2$ equals $P_{SET}$. Thus, for present purposes, in which a feedback control is used, the pressure measured by pressure sensor 22 ($P_2$) and the pressure to be delivered to the patient $P_{SET}$ are interchangeable.

Unlike a conventional pressure support system, one embodiment of the present invention provides a first pressure sensor 30 that measures the inlet pressure $P_1$ to valve 13, which is also the output pressure of pressure generator 12. The output of pressure sensor 30 is provided to controller 24.

Controller 24 regulates the operating speed of pressure generator 12 based on the output of pressure sensor 30 and the output of pressure sensor 22 ($P_2$) or based on the pressure to be delivered to the patient ($P_{SET}$). More specifically, controller 24 adjusts the operating speed, and hence the output pressure $P_1$, of pressure generator 12 to provide the lowest possible "overhead pressure", while still meeting the pressure therapy needs of the patient, i.e., while still ensuring that the patient receives a pressure at a level that corresponds to $P_{SET}$. The "overhead pressure" is the pressure that must be delivered to the valve in order for the valve to provide the desired or prescribed pressure level to the patient's airway in accordance with his or her pressure support therapy. In practice, the "overhead pressure" $P_{OH}$ is the difference between the pressure measured by the pressure sensor 30 and pressure sensor 22, so that $P_{OH}=P_1-P_{SET}$. Because the controller regulates valve 13 so that the pressure at the output of the valve $P_2$ corresponds to $P_{SET}$, the overhead pressure can also be described as $P_{OH}=P_1-P_2$.

Conceptually, controller 24 is performing two pressure control operations:

(1) one based on the pressure to be delivered to the patient $P_{SET}$ (which can be CPAP, bi-level, auto-titrating, PPAP, PAV, or any other pressure waveform); and (2) one based on the overhead pressure $P_{OH}$ needed to ensure that the minimum overhead pressure is provided to the valve, while the pressure support system still provides the pressure to the airway of the patient at a level that is sufficient to meet his or her prescribed or therapeutic need. It should be noted that these two control operations can be carried out independently using separate processing elements or carried out by a common processing element programmed to perform both control operations.

Figure 3A:
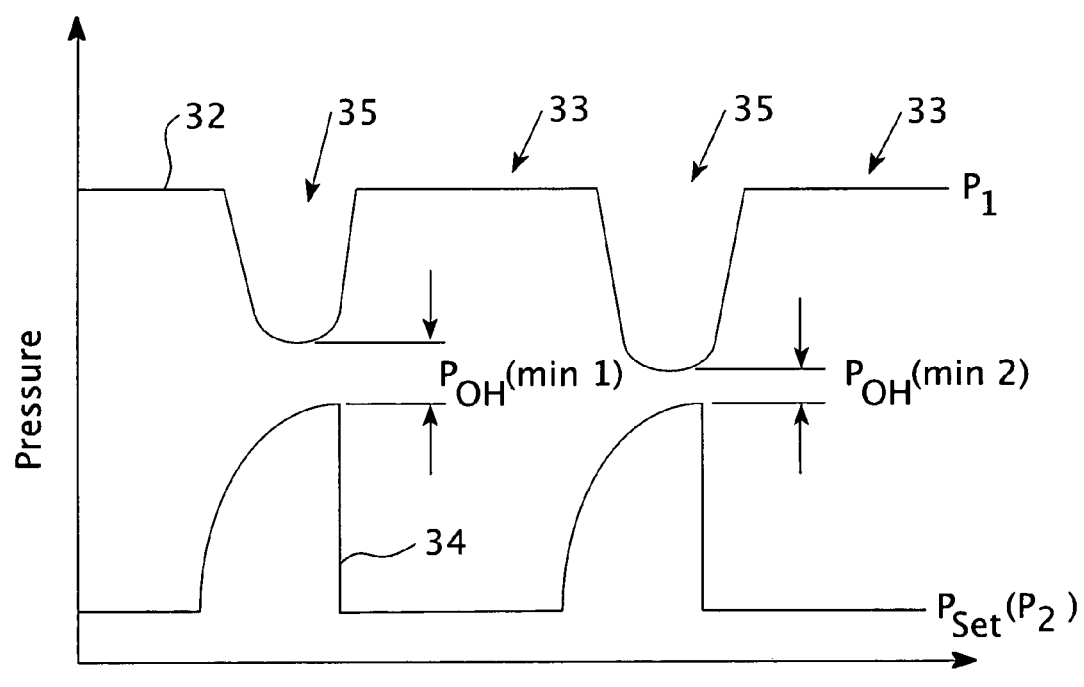
FIGS. 3A and 3B are exemplary pressure and flow graphs illustrating the operation of the system of FIG. 2.
Figure 3B:
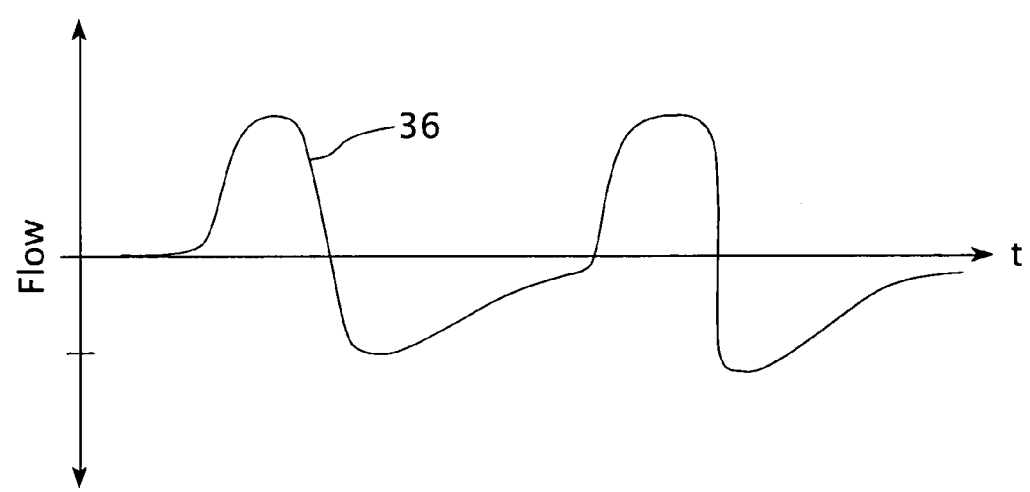

FIGS. 3A–4D are graphs illustrating the pressure control process using pressure sensors 30 and 22 and controller 24 according to the principles of the present invention. FIGS. 3A and 3B illustrate the following: a typical pressure curve 32 for pressure $P_1$ measured by pressure sensor 30, a typical pressure curve 34 for pressure $P_{SET}$ (which, as noted above, corresponds to pressure $P_2$ measured by pressure sensor 22), and a typical flow waveform 36 measured by flow sensor 20 (if used). In these figures, a bi-level pressure support therapy is being provided by the pressure support system.

It can be appreciated from reviewing FIG. 3A, that the overhead pressure $P_{OH}$, is relatively large during the expiratory phase of the breathing cycle, as indicated generally at 33, and is relatively small during the inspiratory phase, as indicated at 35. The present invention seeks to ensure that a sufficient pressure is provided to the inlet of the valve so that the pressure $P_{SET}$ at the outlet of the valve can be maintained, thus ensuring that the patient receives their therapeutic pressure while maximizing the operating efficiency of the pressure support system. Therefore, it is only important that the pressure $P_1$ at the inlet of the valve during the inspiratory phase be considered in order to achieve this function. For this reason, in an exemplary embodiment, the controller monitors the overhead pressure $P_{OH}$ ($P_1-P_{SET}$) to detect the minimum overhead pressure $P_{OH}$(min), which occurs only during the inspiratory phase 35. Detecting the minimum overhead pressure can be accomplished using any conventional detection technique. It can be appreciated from FIG. 3A, that the overhead pressure is at a minimum during the inspiratory phase 35 of the patient's respiratory cycle, when the pressure support system controls the pressure delivered to the airway of the patient to the IPAP level. See $P_{OH}$(min1) and $P_{OH}$(min2) in FIG. 3A.

This minimum overhead pressure $P_{OH}$(min) is preferably compared to a target overhead pressure $P_{OH}$(target). For example, the present invention contemplates providing a target overhead pressure $P_{OH}$(target) of 6 cmH$_2$O. If the minimum overhead pressure $P_{OH}$(min) is outside an error band from the target overhead pressure $P_{OH}$(target), controller 24 adjusts the operating speed of pressure generator 12 in a feedback fashion to bring the minimum overhead pressure $P_{OH}$(min) back to the target overhead pressure $P_{OH}$(target). In an exemplary embodiment of the present invention, the error band around the target overhead pressure $P_{OH}$(target) is ±0.5 cmH$_2$O.

It is to be understood, that this specific target overhead pressure $P_{OH}$(target) and the range for the error band can be other values. Moreover, the target overhead pressure $P_{OH}$(target) and the range for the error band can be adjusted either manually or automatically to achieve the desired range of control for the pressure support system. It is to be further understood that the error band can be eliminated entirely.

FIGS. 4A and 4B illustrate a situation where the minimum overhead pressure $P_{OH}$(min) has fallen outside the error band for the target overhead pressure $P_{OH}$(target), as generally indicated at 40, during a first inspiratory phase ($I_1$). This can occur, for example, if the air density in which the pressure support system is operating has changed, for example, if the unit is moved to a higher elevation or if the ambient barometric pressure has dropped. This can also occur if the leakage of gas from the pressurized system is increased, e.g., the patient has moved causing a leak between the mask seal (cushion) and the surface of the patient, or if the patient has taken a relatively large inspiratory breath, such as a large sigh. When this occurs, the efficiency of the pressure generator is reduced so that the output pressure $P_1$ is not as high as it was at the lower elevation, higher barometric pressure, less system leak, and/or smaller inspiratory breath.

Figure 5A:
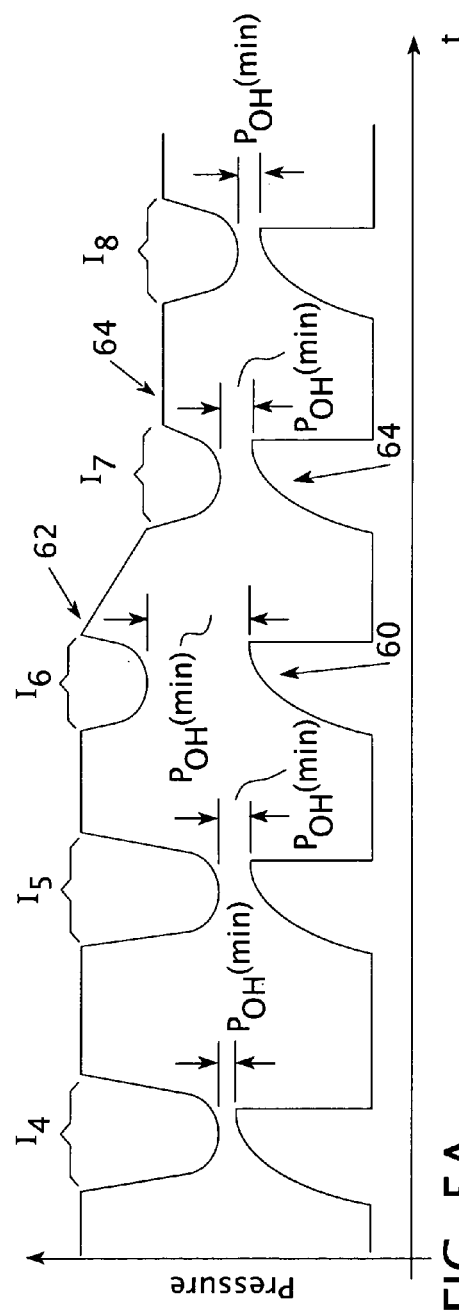

When the controller determines that the minimum overhead pressure $P_{OH}$(min) does not correspond to the target overhead pressure $P_{OH}$(target), controller 24 begins increasing the motor speed, as indicated generally at 42. The increase in motor speed translates into an increase in pressure level $P_1$ beginning at 42. During the next inspiratory phase ($I_2$), the minimum overhead pressure $P_{OH}$(min) detected during that phase is again compared to the target overhead pressure $P_{OH}$(target). As generally indicated at 44, the minimum overhead pressure $P_{OH}$(min) is still less than the target overhead pressure $P_{OH}$(target). Thus, the motor speed is again increased (or continues to be increased) as indicated at 46. During the third inspiratory phase ($I_3$), the minimum overhead pressure $P_{OH}$(min) is no longer less than the target overhead pressure $P_{OH}$(target), as indicated at 48. Thus, the motor speed is held constant, as indicated at 50. Of course, if the minimum overhead pressure $P_{OH}$(min) should increase above the target overhead pressure $P_{OH}$(target), the motor speed is decreased. An example of this is shown in FIG. 5A. Again, it is to be understood, that if an error band is used with the target overhead pressure $P_{OH}$(target), the minimum overhead pressure $P_{OH}$(min) must fall outside this error band before a motor speed adjustment is made.

The present invention contemplates that the rate at which the speed of the motor in the pressure generator is changed can be fixed or variable. For example, the rate at which the motor speed is increased (or decreased) can be based on the amount of difference between the minimum overhead pressure $P_{OH}$(min) and the target overhead pressure $P_{OH}$(target). Thus, the further the minimum overhead pressure $P_{OH}$(min) is below the target overhead pressure $P_{OH}$(target), the more the speed is increased. When using a fixed rate of change in motor speed, the rate of change can be set to be relatively fast or relatively slow, depending on the tradeoffs the user is willing to accept. A relatively fast rate of change allows the system to quickly correct the pressure overhead error. However, it is believed that corrections in pressure made too rapidly can be detected by the patient using the system, thereby jeopardizing their comfort with the system. In a preferred embodiment of the present invention, the rate of change is set such that it takes approximately 10 breaths for the system to transition from a $P_{OH}$ of 0 cmH$_2$O to a $P_{OH}$ of 6 cmH$_2$O.

In the illustrated embodiment, the motor speed of the pressure generator is adjusted (increased or decreased) at the start of the expiratory phase following the inspiratory phase in which the need for an adjustment was detected. This is so because in this embodiment, the controller first searches for the minimum overhead pressure. $P_{OH}$(min) during the inspiratory phase and uses this value compared to the threshold to determine whether or not to adjust the output pressure $P_1$. It is to be understood, however, that other techniques of controlling the motor speed, and hence, the output pressure $P_1$ are contemplated by the present invention. For example, the present invention contemplates continuously monitoring the overhead pressure ($P_1$-$P_{SET}$) during the inspiratory phase and increasing the operating speed immediately when the overhead pressure falls below the minimum pressure threshold $P_{min}$.

In the embodiment illustrated in FIG. 4A, during inspiratory phase $I_1$, the output pressure $P_1$ is actually below the set pressure $P_{SET}$ to be delivered to the patient. As noted above, the set pressure $P_{SET}$ corresponds to the pressure that the system is supposed to be delivering to the patient, such as the CPAP pressure or the IPAP pressure. This means, that even if valve 13 is fully closed so that no gas flows to atmosphere and all gas generated by the pressure generator is communicated by the valve to the patient circuit, the pressure of gas $P_2$ being delivered to the patient is below that which he or she is supposed to be receiving. The present invention contemplates two techniques for dealing with this situation. It should be noted that regardless of the technique used, the pressure delivered to the patient $P_2$ will not meet the set pressure until the motor speed (output pressure $P_1$ from the pressure generator) is increased.

According to a first technique, the pressure to be delivered to the patient $P_{SET}$ is allowed to be equal to the pressure delivered to the valve $P_1$ (less whatever small pressure drop may occur in the valve). In short, $P_2$ or $P_{SET}$=$P_1$. The disadvantage of this technique is that it requires, by definition, that valve 13 move to its fully actuated position so that no gas flows to atmosphere and all gas generated by the pressure generator is communicated by the valve to the patient circuit. This is typically referred to as allowing the valve to "hit the rail"—where the physical constraints of the valve prevent it from opening a path from the pressure generator to the patient circuit any wider. To ensure that valve 13 operates correctly over a long period of time, it is preferable to avoid allowing the moveable elements of the valve to "hit the rail".

Thus, a second technique, which is shown in FIG. 4A, has been developed for use with the control system of the present invention. According to this technique, when the input pressure to the valve $P_1$ falls below the pressure to be delivered to the patient $P_{SET}$, the pressure to be delivered to the patient $P_{SET}$ is recalculated as follows: $P_{SET}$=$P_1$-k, where k is a constant. Constant k is selected to prevent the valve from being moved to its fully actuated position. Constant k is illustrated graphically in FIG. 4A as a gap 52 between $P_1$ and $P_2$ during inspiratory phase $I_1$.

It is to be understood that other techniques for controlling the pressure so that the valve does not "hit the rail" are contemplated by the present invention. For example, when $P_1$<$P_{SET}$, $P_{SET}$ can be recalculated as a function of the flow in the patient circuit. In one embodiment $P_{SET}$=$P_1$-f(Q), where Q is the rate of fluid flow in the patient circuit, which is typically measured by flow sensor 20. The present invention also contemplates monitoring the position of the valve an controlling its actuation so that it does not "hit the rail" by adjusting $P_{SET}$ accordingly to achieve this function.

Figure 5B:
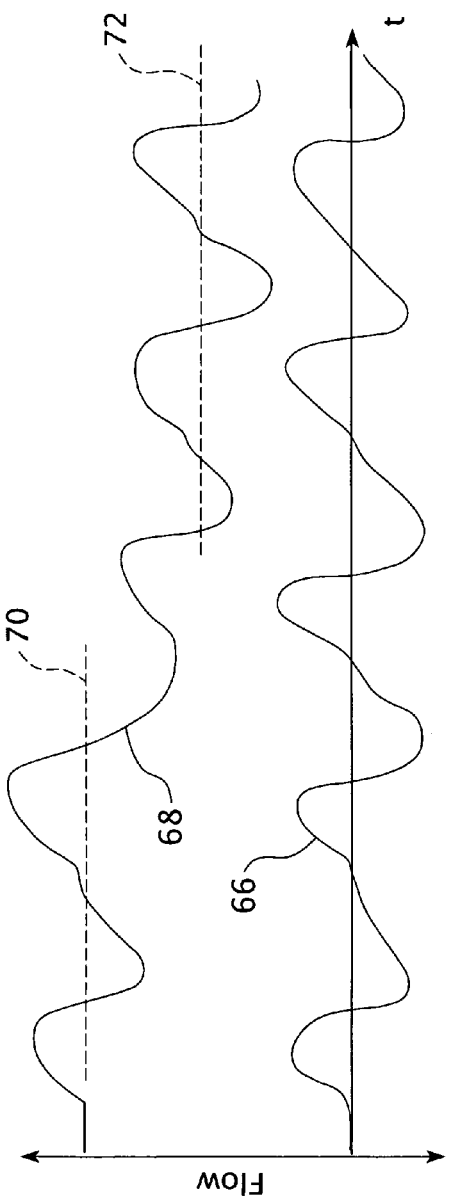

FIGS. 5A and 5B illustrate a situation where the minimum overhead pressure $P_{OH}$(min) is within acceptable levels during inspiratory phases 14 and 15, but has risen above the maximum pressure threshold $P_{max}$, as generally indicated at 60, during inspiratory phase $I_6$. This can occur, for example, if a leak from the pressurized system is decreased or removed, e.g., the patient has adjusted his or her mask to correct a leak between the mask seal (cushion) and the surface of the patient. When this occurs, the head losses in the pressure generator decrease so that the rotating speed of the motor in the pressure generator need not be as high as it was when there was a larger leak When controller 24 determines that the minimum overhead pressure $P_{OH}(min)$ is above the target overhead pressure $P_{OH}(target)$, controller 24 begins decreasing the motor speed, as indicated generally at 62. The decrease in motor speed translates into a decrease in pressure level $P_1$ beginning at 62. During the next inspiratory phase ($I_7$), the minimum overhead pressure $P_{OH}(min)$ detected during that phase is again compared to the target overhead pressure $P_{OH}(target)$. During inspiratory phase $I_7$, the minimum overhead pressure $P_{OH}(min)$ is no longer greater than the target overhead pressure $P_{OH}(target)$. Thus, the motor speed is held constant, as indicated at 64.

FIG. 5B illustrates a patient flow 66, which is the flow of gas into and out of the patient, and a total flow 68, which corresponds to the flow indicated by arrow B in FIG. 2 and is the sum of all flows due to leaks (intentional and unintentional) and the patient flow. FIG. 5B illustrates the drop in flow due to leak from a first level 70 to a second, lower level 72 as a result of the leak correction occurring at 60. Is should be noted that the patient flow 66 remains unchanged despite changes in the leak rate from the pressurized system.

It can be appreciated from the above description that the motor speed control of the present invention provides the same function as a barometric pressure sensor without the additional sensor cost while additionally compensating for all head losses in the system, which cannot be accomplished with a barometric pressure sensor. The present invention also minimizes the output pressure generated by the pressure generator while automatically compensating for pressure losses due to leak, changes in motor efficiency (such as patient breathing in the patient circuit), and changes in the ambient atmosphere. In addition, audible noise from motor vibration is minimized for a given set of atmospheric and patient load conditions.

Figure 6:
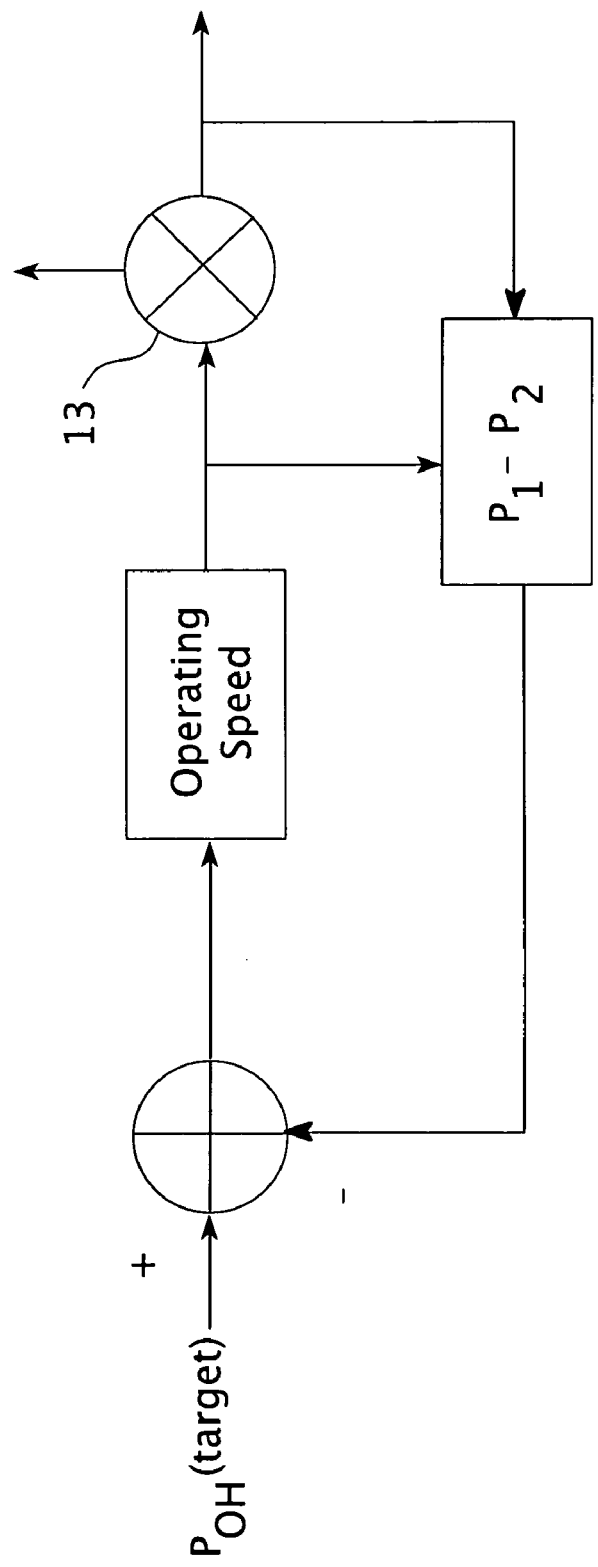
FIG. 6 is a schematic illustration of a feedback control technique according to one embodiment of the present invention.

In the illustrated embodiment, separate pressure sensors 22 and 30 are provided on either side of valve 13. Each pressure sensor 22 and 30 is referenced to atmosphere. It is to be understood, that the present invention also contemplates providing a differential pressure sensor connected across valve 13 to directly measure the overhead pressure. That is each side of the pressure sensor is connected to the patient circuit on each respective side of valve 13. An advantage of using a differential pressure sensor in this configuration is that the differential pressure sensor need not be calibrated to atmospheric pressure. In this embodiment, pressure sensor 22 is still needed in order to ensure that the set pressure, i.e., the desired therapy pressure, is delivered to the patient. FIG. 6 schematically illustrates the feedback control technique for controlling the operating speed of the pressure generator based on pressure $P_1$ measured at the inlet to the exhaust valve and pressure $P_2$ measured at the outlet to the exhaust valve.

It should also be noted that flow sensor 20 is optional. Flow sensor 20 is typically used in pressure support systems that require leak estimation, such as bi-level and auto-titration systems, and systems that control the pressure based at least in part on flow, such as PPAP and PAV systems.

Pressure sensor 22 can be provided anywhere between valve 13 and the patient's airway. If the pressure sensor is connected to the patient circuit at a location that is distal from the patient, as shown in FIG. 2, conventional techniques to estimate the pressure at the airway of the patient, for example, by compensating for the pressure drop along conduit 14, are used.

In the embodiments shown in FIGS. 3A–5B a bi-level mode of pressure support is shown. It is to be understood, however, that the pressure support system of the present invention can provide any type of pressure support. CPAP, bi-level, auto titration, PAV, PPAP, etc., as well as any combination thereof. In addition, the pressure support system can include any conventional devices, such a humidifier, bacterial filters, alarms, compliance monitors, etc., typically used in pressure support systems.

In the embodiment described above this minimum overhead pressure $P_{OH}(min)$ is compared to a target overhead pressure $P_{OH}(target)$, with or without an error band. It is to be understood, however, the present invention contemplates other techniques for controlling the overhead pressure. For example, in another embodiment of the present invention, the minimum overhead pressure $P_{OH}(min)$ is compared to a minimum overhead pressure threshold $P_{OH}(threshold(min))$, a maximum threshold $P_{OH}(threshold(max))$, or both. So long as the minimum overhead pressure $P_{OH}(min)$ remains within these thresholds, the motor speed is not changed. If, however, the minimum overhead pressure $P_{OH}(min)$ falls below the minimum overhead pressure threshold $P_{OH}(threshold(min))$, the output of the pressure generator is increased, and if the minimum overhead pressure $P_{OH}(min)$ rises above the maximum overhead pressure threshold $P_{OH}(threshold(max))$, the output of the pressure generator is decreased. Thus, in this embodiment, the minimum overhead pressure threshold $P_{OH}(threshold(min))$ and maximum threshold $P_{OH}(threshold(max))$ define the boundaries for the fluctuations in the minimum overhead pressure $P_{OH}(min)$.

In the invention described immediately above, the minimum overhead pressure is compared to a maximum threshold level $P_{max}$, and a minimum pressure threshold $P_{min}$ and the output of the pressure generator is adjusted accordingly. It is to be understood, however, that the present invention contemplates comparing the minimum overhead pressure to the minimum pressure threshold $P_{min}$ only. The output of the pressure generator (operating speed) is increased if the minimum overhead pressure falls below the minimum pressure threshold $P_{min}$. To allow for reductions in the output of the pressure generator, the controller can periodically decrease the output (reduce the operating speed) of the pressure generator by some amount. So long as the minimum overhead pressure remains above the minimum pressure threshold $P_{min}$ the reduction is allowed. This process can be repeated so that the system effectively "searches" for the lowest operating speed for the pressure generator while maintaining the minimum overhead pressure remains above the minimum pressure threshold $P_{min}$.

The converse is also possible. That is, the present invention contemplates comparing the minimum overhead pressure to the maximum pressure threshold $P_{max}$ only. The output of the pressure generator (operating speed) is decreased if the minimum overhead pressure is above the maximum pressure threshold $P_{max}$. The controller can periodically increase the output (increase the operating speed) of the pressure generator by some amount. So long as the minimum overhead pressure remains below the maximum pressure threshold $P_{max}$ the increase is allowed. This process can be repeated so that the system effectively "searches" for the highest operating speed for the pressure generator while maintaining the minimum overhead pressure remains below the maximum pressure threshold $P_{max}$.

In addition to or in place of controlling the operating speed of the pressure generator to ensure that an acceptable overhead pressure is maintained, the present invention also contemplates controlling the operating speed of the pressure generator based on other criteria. That is, the prevent invention contemplates that the pressure support system monitor a characteristic associated with the pressure regulator, i.e., the valve, the fluid flow downstream of the pressure regulator, the fluid flow upstream of the pressure regulator, the fluid flow exhausted from the pressure regulator, or any combination thereof. The controller then controls an operating speed of the pressure generator based on the monitored characteristic(s) so that the output of the pressure generator is only kept as high as needed to provide the desired pressure to the patient.

In one embodiment of the present invention, the preset invention contemplates controlling the operating speed of the blower based on the exhaust flow from the patient circuit via valve 13. For example, a flow sensor can be provided to detect the flow of exhaust gas C (see FIG. 2) and provide a feedback signal to controller 24. The controller adjusts the operating speed to the pressure generator to minimize the exhaust or wasted flow dumped from the patient circuit.

In another embodiment of the present invention, the shape of the pressure waveform at the outlet of the valve, as the patient, or at both locations are monitored. The operating speed of the pressure generator is adjusted minimize any error or difference between the desired therapy pressure waveform and the measured therapy pressure waveform. For example, the shape of waveform $P_{SET}$ (i.e., $P_2$) is monitored. As shown in FIG. 4A, if the pressure overhead becomes to small, the waveform shape changes, as is the case during inspiratory cycle $I_1$. The present invention contemplates detecting the deviations of the waveform to be delivered to the patient from an model waveform or from expected values of the waveform, such as peak values, and adjusting the operating speed of the pressure generator to correct for these deviations. This embodiment has the advantage in that only one pressure sensor is needed at the outlet of the valve, and no pressure sensor is need at the valve inlet.

Still another embodiment of the present invention contemplates providing a flow sensor on the valve inlet and a flow sensor on the valve outlet. The operating speed of the pressure generator is adjusted so that the flow measured by both flow sensors during the inspiratory phase, i.e., during the IPAP therapy level in a bi-level system, is nearly equal.

Yet another embodiment of the present invention contemplates monitoring the patients flow waveform and adjusting the operating speed of the pressure generator to provide the maximum inspired tidal volume for a given pressure therapy.

Another embodiment of the present invention contemplates monitoring the patient's flow and adjusting the operating speed of the pressure generator to provide to provide the maximum peak inspired flow for a given pressure therapy.

A still further embodiment of the present invention contemplates monitoring the movement of valve 13. The operating speed of the pressure generator is adjusted to insure that the valve is traversing the entire stroke, i.e., is operating over its entire range of movement.

A further embodiment of the present invention that is related to the immediately preceding embodiment contemplates monitoring the valve current, i.e., the energy provided to the valve 13, or other characteristics associated with the movement of the valve. The operating speed of the pressure generator is adjusted to insure that the valve current (or other movement characteristic) is maximized.

Yet another embodiment of the present invention contemplates monitoring a control parameter, e.g. the integrator term in a PID, for the valve controller. The operating speed of the pressure generator is adjusted to minimize the integral term.

Still another embodiment of the present invention, contemplates providing a microphone or (accelerometer) on the pressure generator and adjusting the operating speed of the pressure generator to minimize the sound pressure level or amplitude of vibration produced by the pressure generator while still maintaining the outlet pressure therapy $P_{SET}$.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

The invention claimed is:

1. A pressure support system comprising:
   a pressure generator adapted to generate a flow or fluid at a pressure above atmospheric pressure;
   a conduit having a first end coupled to the output of the pressure generator and a second end;
   a first pressure sensor operatively coupled to the conduit at a first location;
   a valve operatively coupled to the conduit between the first pressure sensor and the second end of the conduit, wherein the valve is adapted to control a pressure of fluid delivered to the second end of the conduit;
   a second pressure sensor coupled to the conduit at a second location between the valve and the second end of the conduit; and
   a controller operatively coupled to the pressure generator, the valve, and the first pressure sensor, wherein the controller controls actuation of the valve based on a set pressure to be delivered to a patient, which is a pressure measured by the second pressure sensor, and wherein the control ter controls an operating speed of the pressure generator based on an output of the first pressure sensor and the set pressure.

2. The system of claim 1, wherein the first pressure sensor and the second pressure sensor are defined by a differential pressure sensor having a first pressure portion that corresponds to a pressure in the conduit at the first location and a second pressure portion that corresponds to a pressure in the conduit at the second location, wherein the differential pressure sensor monitors a pressure between the first pressure portion and the second pressure portion as the pressure difference.

3. The system of claim 1, further comprising an input device operative coupled to the controller, wherein the set pressure is determined based on an input from the input device.

4. The system of claim 1, wherein the pressure generator comprises an impeller and a motor operatively coupled to the impeller such that operation of the motor rotates the impeller, and wherein the controller controls an operating speed of the motor.

5. The system of claim 1, further comprising a patient interface device coupled to the second end of the conduit.

6. The system of claim 1, wherein the set pressure includes an inspiratory positive airway pressure (IPAP) during at least a portion of an inspiratory phase of a respiratory cycle and an expiratory positive airway pressure (EPAP) during at least a portion of an expiratory phase of the respiratory cycle, and wherein the IPAP level is greater than the EPAP level.

7. The system of claim 2, wherein the set pressure includes an inspiratory positive airway pressure (IPAP) during at least a portion of an inspiratory phase of a respiratory cycle and an expiratory positive airway pressure (EPAP) during at least a portion of an expiratory phase of the respiratory cycle, and wherein the IPAP level is greater than the EPAP level.

8. A pressure support system comprising:
a pressure generator adapted to generate a flow of fluid at a pressure above atmospheric pressure;
a conduit having a first end coupled to the output of the pressure generator and a second end;
a first pressure sensor operatively coupled to the conduit at a first location;
a valve operatively coupled to the conduit, wherein the valve is adapted to control a pressure of fluid delivered to the second end of the conduit; and
a controller operatively coupled to the pressure generator, the valve, and the first pressure sensor, wherein the controller controls actuation of the valve based on a set pressure to be delivered to a patient, wherein the controller controls an operating speed of the pressure generator based on an output of the first pressure sensor and the set pressure, and wherein the controller monitors an overhead pressure as a difference between a pressure measured by the first pressure sensor and the set pressure, and controls the pressure generator based on the overhead pressure.

9. The system of claim 8, wherein the controller compares the overhead pressure to a minimum pressure threshold $P_{min}$ and increases an operating speed of the pressure generator responsive to the overhead pressure being less than the minimum pressure threshold $P_{min}$.

10. The system of claim 8, wherein the controller determines a minimum overhead pressure during an inspiratory phase of such a patient, compares the minimum overhead pressure to a minimum pressure threshold $P_{min}$ and increases an operating speed of the pressure generator responsive to the overhead pressure being less than the minimum pressure threshold $P_{min}$.

11. The system of claim 8, wherein the controller determines a minimum overhead pressure during an inspiratory phase of such a patient, compares the minimum overhead pressure to a maximum pressure threshold $P_{max}$ and decreases an operating speed of the pressure generator responsive to the minimum overhead pressure being greater than the maximum pressure threshold $P_{max}$.

12. The system of claim 8, wherein the controller compares the overhead pressure to a target overhead pressure $P_{OH}(\text{target})$ and adjusts an operating speed of the pressure generator to cause the overhead pressure to correspond to the target overhead pressure $P_{OH}(\text{target})$.

13. The system of claim 8, her comprising a second pressure sensor coupled to the conduit at a second location, and wherein the set pressure is a pressure measured by the second pressure sensor.

14. The system of claim 8, further comprising an input device operative coupled to the controller, wherein the set pressure is determined based on an input from the input device.

15. A pressure support system comprising:
a pressure generator adapted to generate a flow of fluid at a pressure above atmospheric pressure;
a conduit having a first end coupled to the output of the pressure generator and a second end;
a valve operatively coupled to the conduit and adapted to control a pressure of the flow of fluid delivered to such a patient;
first controlling means operatively coupled to the valve for controlling the valve to deliver so that a pressure delivered to an airway of a patient corresponds to a set pressure; and
second controlling means operatively coupled to the pressure generator for controlling an operating speed of the pressure generator to provide a pressure at an inlet of the valve at a level sufficient to deliver the set pressure.

16. The system of claim 15, wherein the first controlling means and the second controlling means are defined by a common processing element.

17. The system of claim 15, further comprising pressure monitoring means for determining a pressure at an inlet of the valve, and wherein the second controlling means controls the operating speed based on an output of the pressure monitoring means.

18. The system of claim 15, further comprising pressure monitoring means for determining a pressure difference across the valve, and wherein the second controlling means controls an operating speed of the pressure generating means based on the pressure difference.

19. The system of claim 15, further comprising a patient interface device coupled to the second end of the conduit.

20. The system of claim 15, wherein the first controlling means provides an inspiratory positive airway pressure (IPAP) during at least a portion of an inspiratory phase of a respiratory cycle and an expiratory positive airway pressure (EPAP) during at least a portion of an expiratory phase of the respiratory cycle, and wherein the IPAP level is greater than the EPAP level.

21. The system of claim 15, wherein the second controlling means determines an overhead pressure across the valve and compares the overhead pressure to a target overhead pressure $P_{OH}(\text{target})$, and adjusts the operating speed of the pressure generator to cause the overhead pressure to correspond to the target overhead pressure $P_{OH}(\text{target})$.

22. The system of claim 15, wherein the second controlling means determines a minimum overhead pressure during an inspiratory phase of such a patient compares the minimum overhead pressure to a maximum pressure threshold $P_{max}$ and decreases an operating speed of the pressure generating means responsive to the minimum overhead pressure being greater than the maximum pressure threshold $P_{max}$.

23. The system of claim 15, wherein the second controlling means determines a minimum overhead pressure during an inspiratory phase of such a patient, compares the minimum overhead pressure to a minimum pressure threshold $P_{min}$ and increases an operating speed of the pressure generating means responsive to the minimum overhead pressure being less than the minimum pressure threshold $P_{min}$.

24. A method of providing pressure support to a patient comprising:
generating a flow of fluid at a pressure above atmospheric pressure via a pressure generator;
providing the flow of fluid to a patient;
controlling a pressure of the flow of fluid delivered to such a patient via a pressure control element so that a pressure delivered to an airway of a patient corresponds to a set pressure; and
controlling an operating speed of the pressure generator to provide a pressure at an inlet of the pressure control element at a level sufficient to deliver the set pressure.

25. The method of claim 24, further monitoring a pressure at an inlet of the pressure control element, and wherein controlling the operating speed is done based the monitored pressure.

26. The method of claim 24, further monitoring a pressure difference across the pressure control element, and wherein controlling the operating speed is done based on the pressure difference.

27. The method of claim 26, wherein controlling the operating speed includes comparing the pressure difference to a threshold level and controlling the pressure generator based on the comparison.

28. The method of claim 24, wherein controlling a pressure of the flow of fluid delivered to such a patient via a pressure control element includes providing the flow of fluid at an inspiratory positive airway pressure (IPAP) during at least a portion of an inspiratory phase of a respiratory cycle and at an expiratory positive airway pressure (EPAP) during at least a portion of an expiratory phase of the respiratory cycle, and wherein the IPAP level is greater than the EPAP level.

29. The method of claim 24, wherein controlling the operating speed of the pressure generator includes determining an overhead pressure across the pressure control element, comparing the overhead pressure to a target overhead pressure $P_{OH}$(target), and adjusts the operating speed of the pressure generator to cause the overhead pressure to correspond to the target overhead pressure $P_{OH}$(target).

30. The method of claim 24, wherein controlling the operating speed of the pressure generator includes determining a minimum overhead pressure during an inspiratory phase of such a patient, comparing the minimum overhead pressure to a maximum pressure threshold $P_{max}$, and decreasing the operating speed of the pressure generator responsive to the minimum overhead pressure being greater than the maximum pressure threshold $P_{max}$.

31. The method of claim 24, wherein controlling the operating speed of the pressure generator includes determining a minimum overhead pressure during an inspiratory phase of such a patient, comparing the minimum overhead pressure to a minimum pressure threshold $P_{min}$, and increasing the operating speed of the pressure generator responsive to the minimum overhead pressure being less than the minimum pressure threshold $P_{min}$.

* * * * *